US007400757B2

(12) United States Patent
Jolly et al.

(10) Patent No.: US 7,400,757 B2
(45) Date of Patent: Jul. 15, 2008

(54) SYSTEM AND METHOD FOR SEGMENTING THE LEFT VENTRICLE IN A CARDIAC IMAGE

(75) Inventors: Marie-Pierre Jolly, Hillsborough, NJ (US); Ying Sun, Plainsboro, NJ (US); Nicolae Duta, Medford, MA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 262 days.

(21) Appl. No.: 11/049,188

(22) Filed: Feb. 2, 2005

(65) Prior Publication Data

US 2005/0238215 A1    Oct. 27, 2005

Related U.S. Application Data

(63) Continuation-in-part of application No. 09/970,552, filed on Oct. 4, 2001, now Pat. No. 6,961,454.

(51) Int. Cl.
*G06K 9/00*     (2006.01)
(52) U.S. Cl. .................................................... 382/131
(58) Field of Classification Search .................. 382/131
See application file for complete search history.

(56) References Cited

U.S. PATENT DOCUMENTS

| 5,239,591 | A | * | 8/1993 | Ranganath | ................... | 382/128 |
| 5,457,754 | A | * | 10/1995 | Han et al. | ................... | 382/128 |
| 5,570,430 | A | * | 10/1996 | Sheehan et al. | ............. | 382/128 |
| 5,669,382 | A | * | 9/1997 | Curwen et al. | .............. | 600/425 |
| 5,754,676 | A | * | 5/1998 | Komiya et al. | .............. | 382/132 |
| 5,768,413 | A | * | 6/1998 | Levin et al. | ................. | 382/173 |
| 6,078,688 | A | * | 6/2000 | Cox et al. | ................... | 382/173 |
| 6,795,521 | B2 | * | 9/2004 | Hsu et al. | ....................... | 378/4 |

FOREIGN PATENT DOCUMENTS

| WO | WO 03/029831 A | 4/2003 |
| WO | WO 2004/068406 A | 8/2004 |

OTHER PUBLICATIONS

Ranganath, S. "Contour Extraction from Cardiac MRI Studies Using Snakes", Jun. 1995, IEEE Transactions on Medical Imaging, vol. 14, No. 2, p. 328-338.*

(Continued)

*Primary Examiner*—Vikkram Bali
*Assistant Examiner*—Katrina Fujita
(74) *Attorney, Agent, or Firm*—Donald B. Paschburg; F. Chau & Associates, LLC (57) ABSTRACT

A method is provided for segmenting an image of interest of a left ventricle. The method includes determining a myocardium contour according to a graph cut of candidate endocardium contours, and a spline fitting to candidate epicardium contours in the absence of shape propagation. The method further includes applying a plurality of shape constraints to candidate endocardium contours and candidate epicardium contours to determine the myocardium contour, wherein a template is determined by shape propagation of a plurality of images in a sequence including the image of interest in the presence of shape propagation.

19 Claims, 6 Drawing Sheets

OTHER PUBLICATIONS

Blimes, J. "A Gentle Tutorial of the EM Algorithm and its Application to Parameter Estimation for Gaussian Mixture and Hiddon Markov Models", Apr. 1998, UC Berkley, TR-97-021, p. 1-13.*

Higgins et al., "Extraction of Left-Ventricular Chamber from 3-D CT Images of the Heart", Dec. 1990, IEEE Transactions on Medical Imaging, vol. 9, No. 4, 384-395.*

John (Juyang) Weng et al: "Learning—Based Ventricle Detection from Cardiac MR and CT Images" IEEE Transactions on Medical Imaging, IEEE Service Center, Piscataway, NJ, US, vol. 16, No. 4, Aug. 1997, XP011035650 ISSN: 0278—0062 cited in the application abstract sections I.D., II and IV.

Bankman I et al: "Two—Dimensional Shape and Texture Quantification" Handbook of Medical Imaging Processing and Analysis, 2000, pp. 215-230, XP002249040 sections 1.1 and 1.2.

\* cited by examiner

SYSTEM AND METHOD FOR SEGMENTING THE LEFT VENTRICLE IN A CARDIAC IMAGE

CROSS-REFERENCE TO RELATED APPLICATIONS

This is a continuation-in-part application of U.S. application Ser. No. 09/970,552, filed Oct. 4, 2001, now U.S. Pat. No. 6,961,454 entitled "System and Method for Segmenting the Left Ventricle in a Cardiac MR Image", the disclosure of which is herein incorporated by reference in its entirety.

BACKGROUND OF THE INVENTION

1. Technical Field

The present disclosure relates to medical imaging, and more particularly to extracting the myocardium from four-dimensional image data (two-dimensional images over time and space).

2. Discussion of Related Art

Cardiovascular disease is the leading cause of death in the United States. Mortality has been declining over the years as lifestyle has changed, but the decline is also due to the development of new technologies to diagnose disease. One of these techniques is magnetic resonance imaging (MRI), which provides time-varying three-dimensional imagery of the heart. To help in the diagnosis of disease, physicians are interested in identifying heart chambers, the endocardium and epicardium, and measuring changes in ventricular blood volume (ejection fraction) and wall thickening properties over a cardiac cycle. The left ventricle is of particular interest since it pumps oxygenated blood out to distant tissue in the entire body.

There has been a large amount of research on the analysis of medical images. Segmentation of these images has been particularly challenging. In the early nineties, researchers realized that tracking the cardiac wall motion in MR images could be used to characterize meaningful functional changes. A system proposed by S. R. Fleagle, D. R. Thedens, J. C. Ehrhardt, T. D. Scholz, and D. J. Skorton, "Automated identification of left ventricular borders from spin-echo resonance images", *Investigative Radiology*, 26:295-303, 1991, delineates the border of the myocardium using a minimum cost path graph search method after a user indicates the center of the left ventricular cavity and an area of interest, for example, with a mouse. D. Geiger, A. Gupta, L. A. Costa, and J. Vlontzos, "Dynamic programming for detecting, tracking, and matching deformable contours", *IEEE Trans. PAMI*, 17(3): 294-302, 1995, used a dynamic programming approach to refine the contours specified by the user. A. Goshtasby and D. A. Turner, "Segmentation of cardiac cine MR images for extraction of right and left ventricular chambers", *IEEE Trans. Medical Imaging*, 14(1):56-64, 1995, proposed a two step method combining intensity thresholding to recover blood from an image and a local gradient to outline strong edges using elastic curves. J. Weng, A. Singh, and M. Y. Chiu, "Learning-based ventricle detection from cardiac MR and CT images", *IEEE Trans. Medical Imaging*, 16(4):378-391, 1997, applied a threshold to an image based on parameters estimated during a learning phase to approximate the segmentation.

However, no known system or method exists for providing an adaptive technique of analyzing cardiac images. Therefore, a need exists for a method of cardiac segmentation combining edge, region and shape information in a deformable template.

SUMMARY OF THE INVENTION

According to an embodiment of the present disclosure, a method for segmenting an image of interest of a left ventricle includes determining a myocardium contour according to a graph cut of candidate endocardium contours, and a spline fitting to candidate epicardium contours in the absence of shape propagation, and applying a plurality of shape constraints to the candidate endocardium contours and the candidate epicardium contours, to determine the myocardium contour, wherein a template is determined by shape propagation of a plurality of images in a sequence including the image of interest, in the presence of shape propagation.

According to an embodiment of the present disclosure, a method for segmenting an image of interest of a left ventricle includes determining a myocardium response image according to a histogram of pixel intensity in the image of interest, determining a plurality of candidate contours, according to a plurality of energy functions, to which a plurality of confidence values are assigned, and applying a plurality of shape constraints to the candidate endocardium contours and the candidate epicardium contours to determine a myocardium contour.

The myocardium contour is based on a plurality of images in a sequence including the image of interest, wherein the myocardium contour includes an endocardium contour and an epicardium contour.

The method comprises determining an approximate contour pair of the left ventricle comprising removing a connected component below a grey level threshold, and determining features of a connected component above the grey level threshold. The method further comprises determining the connected component to be least eccentric, most circular, and most convex among a plurality of connected components above the grey level threshold, approximating the determined connected component as a circle corresponding to a localization of the endocardium, and determining a localization of the epicardium as a circle with the same center and a larger radius as the circle corresponding to the localization of the endocardium.

Determining the myocardium response image according to the histogram of pixel intensity further comprises fitting a mixture of Gaussians to the histogram of pixel intensity to determine portions of blood, muscle and air in the image.

For each candidate closed contour, the method further comprises defining a search space around an approximate contour, defining a line of source nodes and sink nodes, determining a shortest path between the source nodes and the sink nodes, defining a new source node and a plurality of new sink nodes, and determining a shortest path between the new source node and new sink nodes.

The candidate endocardium contours and the candidate epicardium contours are each determined according to a combination of a gradient magnitude and a direction using a cross product of a gradient direction and a contour direction. The method includes determining a first candidate endocardium contour according to a positive cross product of a gradient direction in the input image and a contour direction, determining a second candidate endocardium contour according to a negative cross product of a gradient direction in the myocardium image and a contour direction, determining a first candidate epicardium contour according to a gradient magnitude in the input image, and determining a second candidate epicardium contour according to a positive cross product of a gradient direction in the myocardium image and a contour direction.

The method comprises determining a one-to-one match matrix, wherein points on the endocardium contour and epicardium contour are assigned to a plurality of template points, wherein the template points are determined from propagation through a plurality of images.

According to an embodiment of the present disclosure, a method for segmenting an image of interest of a left ventricle comprises determining a myocardium response image according to a histogram of pixel intensity in the image of interest, determining a plurality of candidate contours, according to a plurality of energy functions, to which a plurality of confidence values are assigned, determining a myocardium contour according to a graph cut of candidate endocardium contours, and a spline fitting to candidate epicardium contours in the absence of shape propagation, and applying a plurality of shape constraints to the candidate endocardium contours and the candidate epicardium contours to determine the myocardium contour, wherein a template is determined by shape propagation of a plurality of images in a sequence including the image of interest, in the presence of shape propagation.

The myocardium contour includes an endocardium contour and an epicardium contour.

The method comprises determining a contour pair of the left ventricle. The method comprises determining a feature of a connected component, the connected component being differentiated from non-cardiac tissue, determining the connected component having a desirable feature among a plurality of connected components differentiated from non-cardiac tissue, approximating the determined connected component as a circle corresponding to a localization of the endocardium, and determining a localization of the epicardium as a circle with the same center and a larger radius as the circle corresponding to the localization of the endocardium.

Determining the myocardium response image according to the histogram of pixel intensity further comprises fitting a mixture of Gaussians to the histogram of pixel intensity to determine portions of blood, muscle and air in the image.

The closed contour includes a plurality of candidate contours, and for each contour, further comprises defining a search space around an approximate contour, defining a line of source nodes and sink nodes, determining a shortest path between the source nodes and the sink nodes, defining a new source node and a plurality of new sink nodes, and determining a shortest path between the new source node and new sink nodes.

The candidate endocardium contour and the candidate epicardium contour are each determined according to a combination of a gradient-magnitude and a direction using a cross product of a gradient direction and a contour direction. The method includes determining a first candidate endocardium contour according to a positive cross product of a gradient direction in the input image and a contour direction, determining a second candidate endocardium contour according to a negative cross product of a gradient direction in the myocardium image and a contour direction, determining a first candidate epicardium contour according to a gradient magnitude in the input image, and determining a second candidate epicardium contour according to a positive cross product of a gradient direction in the myocardium image and a contour direction.

The graph cut further comprises defining a graph wherein each node corresponds to a connected component region between confidence pixels on the candidate contours, and determining a minimum cut between a center node and an outside node.

The spline fitting further comprises fitting a spline through points of the candidate contours.

According to an embodiment of the present disclosure, a program storage device is provided readable by machine, tangibly embodying a program of instructions executable by the machine to perform method steps for segmenting an image of interest of a left ventricle. The method comprising determining a myocardium response image according to a histogram of pixel intensity in the image of interest, determining a plurality of candidate contours, according to a plurality of energy functions, to which a plurality of confidence values are assigned, determining a myocardium contour according to a graph cut of candidate endocardium contours, and a spline fitting to candidate epicardium contours in the absence of shape propagation, and applying a plurality of shape constraints to the candidate endocardium contour and the candidate epicardium contours to determine the myocardium contour, wherein a template is determined by shape propagation of a plurality of images in a sequence including the image of interest, in the presence of shape propagation.

BRIEF DESCRIPTION OF THE DRAWINGS

Preferred embodiments of the present disclosure will be described below in more detail, with reference to the accompanying drawings.

DETAILED DESCRIPTION OF PREFERRED EMBODIMENTS

A system and/or method for segmenting a cardiac image of a left ventricle can be embodied in any suitable commercial cardiac analysis package, such as the ARGUS cardiac analysis package from Siemens, which offers a complete system of drawing tools and automatic segmentation methods to allow the physician to outline the myocardium in each image in the patient data set, determine volumes, ejection fraction, and perform a thickening analysis.

Figure 1:
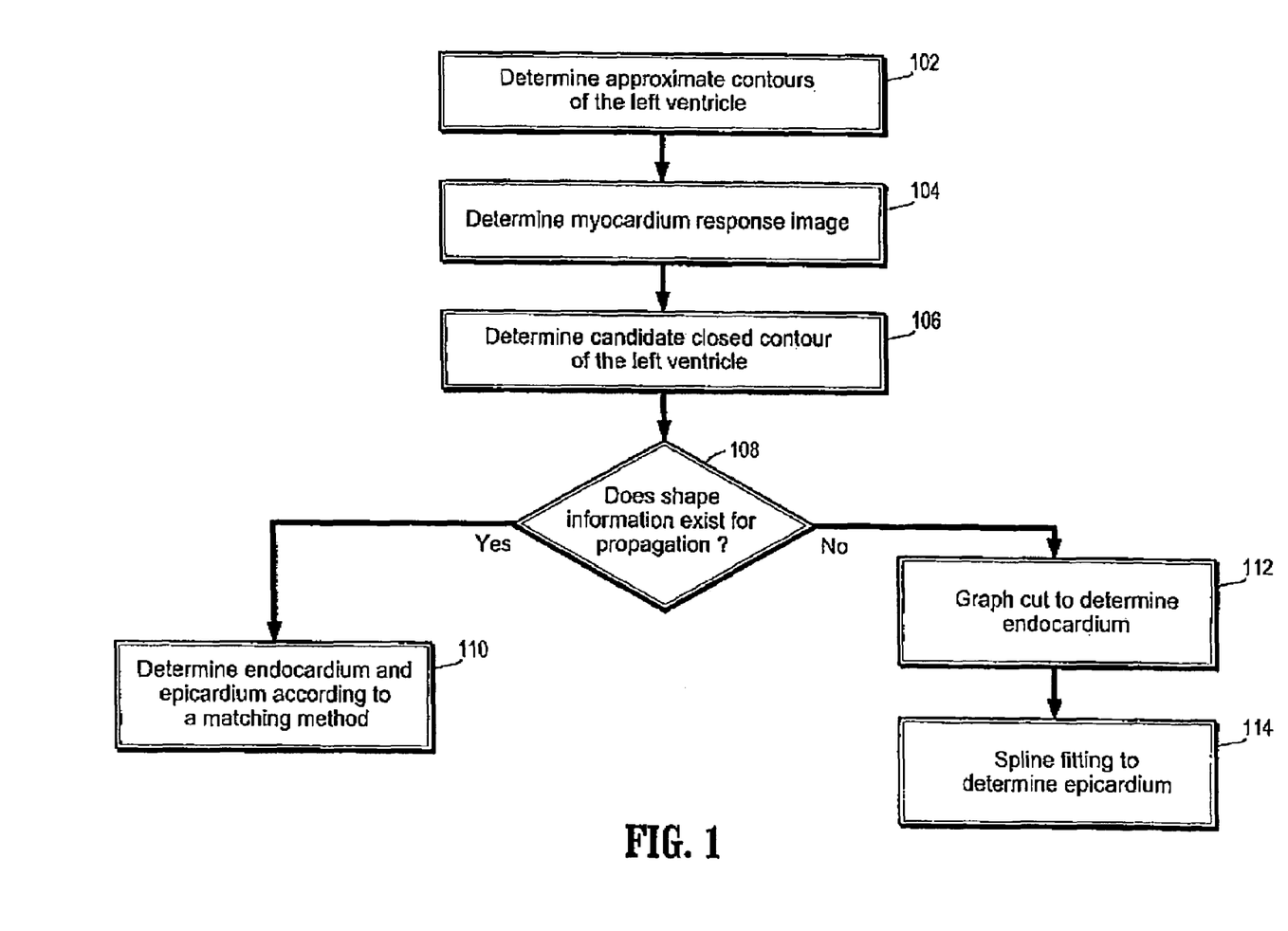
FIG. 1 is a flow chart showing a method of segmentation according to an embodiment of the present disclosure.

Referring to FIG. 1, illustrating a method according to an embodiment of the present disclosure, the method determines approximate contours of the left ventricle 102 and a myocardium response image 104 according to a histogram of pixel intensity in the magnetic resonance image of interest. The method determines a plurality of candidate closed contours of the left ventricle 106, according to a plurality of energy functions. Further, the method is aware of whether shape information exists for the magnetic resonance image of interest 108 and is able to apply a desired method to determine a myocardium image. For example, in the presence of shape information, the method determines a template 110 from propagation through a plurality of magnetic resonance images, and determines an endocardium and epicardium according to a matching technique between the candidate contours and the template. The matching technique can include, for example, point-pattern matching and shape matching. The method determines an endocardium contour according to a graph cut 112 and an epicardium contour according to a spline fitting 114 to the candidate contours for a singular image, where a template is not present.

It is to be understood that the present invention may be implemented in various forms of hardware, software, firmware, special purpose processors, or a combination thereof. In one embodiment, the present disclosure may be implemented in software as an application program tangibly embodied on a program storage device. The application program may be uploaded to, and executed by, a machine comprising any suitable architecture. Preferably, the machine is implemented on a computer platform having hardware such as one or more central processing units (CPU), a random access memory (RAM), and input/output (I/O) interface(s). The computer platform also includes an operating system and micro instruction code. The various processes and functions described herein may either be part of the micro instruction code or part of the application program (or a combination thereof) which is executed via the operating system. In addition, various other peripheral devices may be connected to the computer platform such as an additional data storage device and a printing device.

It is to be further understood that, because some of the constituent system components and method steps depicted in the accompanying figures may be implemented in software, the actual connections between the system components (or the process steps) may differ depending upon the manner in which the present invention is programmed. Given the teachings of the present disclosure provided herein, one of ordinary skill in the related art will be able to contemplate these and similar implementations or configurations of the present invention.

According to an embodiment of the present disclosure, a method is provided which automatically hypothesizes two concentric circles at the location of the left ventricle in an MR image. However, due to the relative symmetry of the left ventricle and computational constraints, the method uses the gray values of the pixels along four cross sections through the ventricle instead of the entire region to determine a feature set. A method of automatic localization is described in entitled, Method for Learning-Based Object Detection in Cardiac Magnetic Resonance Images, and is incorporated by reference herein in its entirety.

According to an embodiment of the present disclosure, a localization patterns a Markov process. A Markov analysis looks at a sequence of events, and analyzes a tendency of an event to be followed by another event, generating a new sequence of random but related events. According to an embodiment of the present disclosure, in a learning phase, positive and negative examples are presented and the method finds the ordering of the Markov process that maximizes a separation (minimizes the Kullbach distance, also known as the relative entropy or cross entropy) between the two classes in the training set. The method includes a detection phase, during which a test image is scanned and each location is assigned to a class based on the log-likelihood ratio.

Neighboring positions classified as the left ventricle are portioned into clusters. The method defines eight salient points in the gray level profiles as the intersection of the four cross sections with the ventricle's medical axis. Average profiles are built from training example profiles aligned using a curve registration technique, for example, as proposed by Ramsay and Xi. The cross sections of each of the cluster candidates are warped onto corresponding average profiles. The location of the salient points in the image are then accumulated using a Hough transform array to vote for the most likely center position and radius for the myocardium centerline.

Typically, the user segments one image, for example, the slice closest to the valves at end-diastole (ED base) and propagates the segmented contours to all the slices in the ED phase (ED propagation). The ED contours can be propagated to the end-systole (ES) phase (ES propagation) to compute the ejection fraction. For a more detailed analysis, the user can also propagate all the ED contours to all the images in all the phases using temporal propagation.

For ED propagation, the automatic localization method described above may be used. However, since the ventricle size is approximately known from the template image, the scale search can be limited, for example, to between 0.85 and 1.15 times the size of the template. The method can limit the search space for the location of the ventricle, for example, to 30 pixels around the location of the template. For ES propagation, the method knows the location of the left ventricle has not changed and therefore, the template contours can be scaled. The endocardium is scaled by 0.6 and the epicardium by 0.9. In the case of temporal propagation, both the location and scale of the contours do not change significantly. Therefore, the method can copy the contours from one image to the next.

Figure 2:
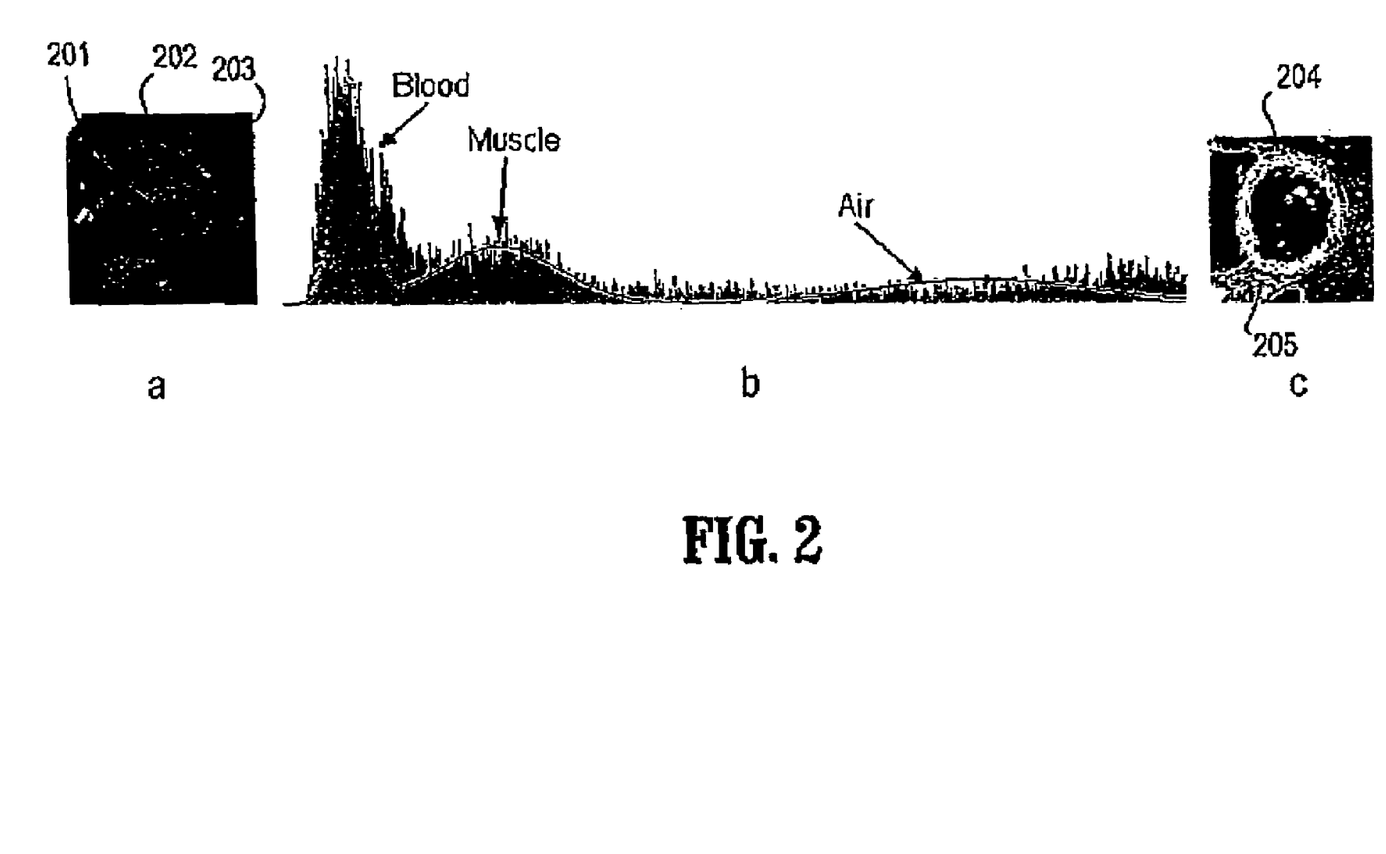
FIG. 2a shows an input image according to an embodiment of the present disclosure.
FIG. 2b shows a histogram of the input image of FIG. 2a, fitted with a mixture of Gaussians according to an embodiment of the present disclosure.
FIG. 2c shows a myocardium response image according to an embodiment of the present disclosure.

In MR imaging, the intensity of a pixel depends on the properties of the tissue being imaged. As shown in FIG. 2a, in an MR image of the left ventricle, the blood is bright 201, the muscles are somewhat dark 202, but not as dark as the air-filed lungs 203. This fact can be verified by looking at the histogram of a region around the myocardium as shown in FIG. 2b. The method uses an Expectation-Maximization (EM) method to fit a mixture of three Gaussians to the histogram. The method then creates a myocardium response image, showing the probability that a pixel belongs to the middle Gaussian which corresponds to the myocardium. It can be seen from FIG. 2c that the left ventricle myocardium 204 is highlighted, but neighboring organs, e.g., 205, are also highlighted.

To complement the results of region segmentation, the method uses an active contour formulation similar to Geiger's dynamic programming approach or Mortensen and Barrett's Dijkstra's approach. The advantage of these graph theoretic methods over a gradient descent approach as proposed by Kass et al. is that they are able to recover the global optimum of the energy function and are therefore insensitive to the initial contour position.

Geiger defines the energy of a contour $(p_1 \ldots p_n)$ as:

$$E(p_1 \ldots p_n) = \sum_{i=1}^{n} \frac{1}{\|\nabla I(p_i)\| + \varepsilon} + \alpha \sum_{i=2}^{n} |\vec{\nabla} I(p_i) - \vec{\nabla} I(p_{i-1})| \quad (1)$$

where $\|\nabla I(p)\|$ is the magnitude and $\vec{\nabla} I(p)$ is the direction of the image gradient at pixel p. This is equivalent to finding a shortest path in a graph where nodes correspond to pixels and the cost of a link between two neighboring pixels is defined as:

$$e(p_1, p_2) = \frac{1}{\|\nabla I(p_2)\| + \varepsilon} + \alpha |\vec{\nabla} I(p_2) - \vec{\nabla} I(p_1)| \quad (2)$$

Figure 3:
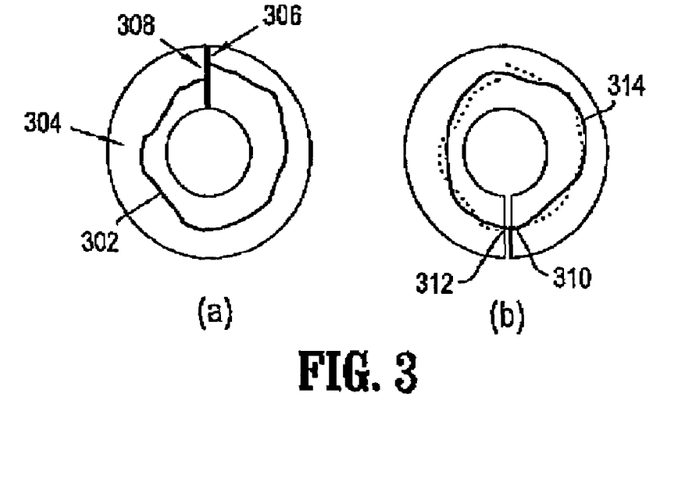
FIGS. 3a-b show an example of two passes of Dijkstra's method according to an embodiment of the present disclosure.

Given an approximate contour in an image, the method places a symmetrical search space 304 around it and defines a line of source nodes 306, connected to a "pseudo" source node, and sink nodes 308. Dijkstra's method then finds the shortest path between the pseudo source node and one of the sink nodes 302. The method defines a new single source point 312 in the middle of the recovered contour and a set of sink nodes 310 neighboring the source node, and does a second pass of Dijkstra's method to produce a closed contour 314.

To combine the information provided by both the image and the myocardium response image, Dijkstra's method is implemented with two different energy functions. Each run gives different candidate points for the contours, along with a confidence based on the contribution of each point to the total energy function. One energy function combines gradient magnitude and direction using the cross product of the gradient direction and the contour direction. In this case, the contour is built clockwise by Dijkstra process and the image gradient points from bright to dark. To separate a bright region inside from a dark region outside, resp. a dark region inside from a bright region outside, the z component of the cross product between the image gradient and the contour direction should be positive, resp. negative. The energy is set to a large number otherwise. The cost of a link between two pixels is:

$$e(I, z > 0, p_1, p_2) = \begin{cases} \frac{1}{\|\nabla I(p_2)\|^2 + \varepsilon} & \text{if } z = \begin{matrix}(x_2 - x_1)\sin(\vec{\nabla} I(p_2)) - \\ (y_2 - y_1)\cos(\vec{\nabla} I(p_2))\end{matrix} > 0 \\ \frac{1}{\varepsilon} & \text{otherwise} \end{cases} \quad (3)$$

where $\varepsilon$ is a small constant, for example, 0.001, to bound the energy function. $E(I, z>0)$ and $E(H, z<0)$ can be used for the endocardium, where I is the input image and H is the myocardium response image. For epicardium, $E(H, z>0)$ can be used. Since the gradient direction in I outside the myocardium flips between the bright right ventricle and the dark lungs, $E'(I)$ can be used, which can be defined as:

$$e'(I, p_1, p_2) = \frac{1}{\|\nabla I(p_2)\|^2 + \varepsilon} \quad (4)$$

Different energy functions highlight different features of the myocardium.

Dijktra's method is applied with various energy functions and all points on the resulting contours are candidate points for the final contour. When the contours are propagated from one image to the next, either spatially or temporally, it is reasonable to assume that the shape of the contours does not change drastically. Based on this assumption, the method can determine which parts of which contours are correct.

A shape alignment method, for example, as proposed by Duta et al., is used to establish a correspondence between a subset $A'$ of the template points $A = \{A_j\}_{j=1, \ldots, a}$ and a subset $B'$ of the candidate test points $B = \{B_k\}_{k=1, \ldots, b}$. According to an embodiment of the present disclosure, both contours are considered as one shape. Given a pair of "corresponding" points in A and B, a rigid similarity transform is hypothesized to align the contours. A one-to-one match matrix M is determined to assign every point B to its closest neighbor in A if the distance is less than a threshold. This allows the following equation:

$$f(M) = \frac{1}{n^2} \sum_{j=1}^{n} \frac{w_j[(x_{A_j} - ax_{B_j} + cy_{B_j} - b)^2 +}{(y_{A_j} - ay_{B_j} + cx_{B_j} - d)]} + \frac{2}{n} \quad (5)$$

where n is the number of correspondences and (a,b,c,d) are the parameters of the similarity transform. The weight $w_j$ is set to be the confidence of the test point $B_j$. The goal is to minimize f(M). It is not possible to evaluate all possible quadruplets of points, so the 10% of the points with the largest confidence in the test set are chosen and paired with points from the same contour in the template set. One of ordinary skill in the art would recognize in light of the present disclosure that larger and smaller sets of points can be chosen.

Figure 4:
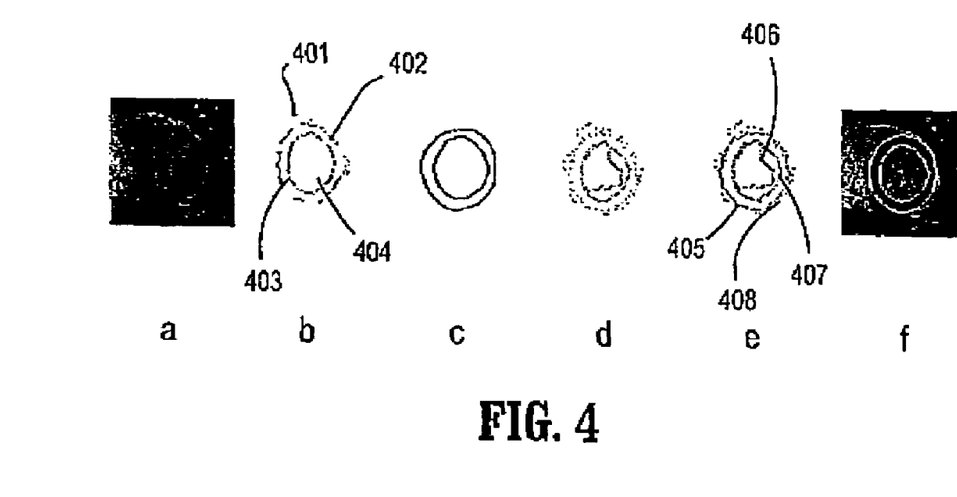
FIGS. 4a-f show an example of applying shape constraints to recover the myocardium contours according to an embodiment of the present disclosure.

FIG. 4a shows the input image and FIG. 4b illustrates four recovered contours, 401-404, where darker points show higher confidence. FIG. 4c shows the template shape from the segmentation of the previous image. FIG. 4d shows the established correspondences for the best similarity transform. The shape constraints allow the method to choose the outside candidate points for the endocardium 407 rather than the inside points that outline the papillary muscles 406, and the inside candidate points for the epicardium 405 rather than the outside points that outlined the fat 408. Once the correspondences are established, the template shape is warped by moving the template points to their corresponding test points as in FIG. 4e. The contours are smoothed using the method proposed by Xu et al., which minimizes shrinkage. A final segmentation result is shown in FIG. 4f.

When an image needs to be segmented on its own, not in the context of propagation, there is no shape information available to the system. The endocardium should be pushed as far as possible away from the center so that it outlines the myocardium rather than the papillary muscles, and the epicardium should stay close the endocardium. To enforce these constraints, the method modifies the confidence values in the following way:

$$C_{endo}(p) = C_{endo}(p) \left( \frac{d(p, \Omega)}{\max_p d(p, \Omega)} \right)^3$$

$$C_{epi}(p) = C_{epi}(p) \left( \frac{d(p, endo)}{\max_p d(p, endo)} \right)^3$$

where $\Omega$ is the center of mass of the confidence points.

Figure 5:
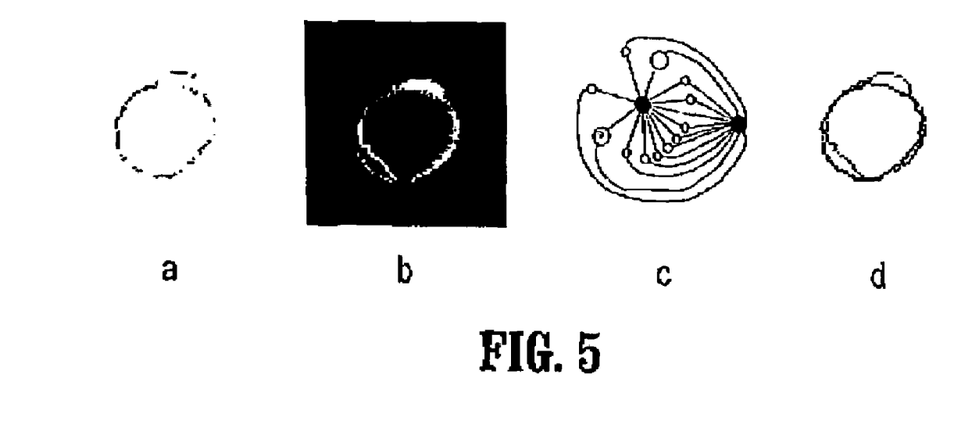
FIGS. 5a-d show an example of a graph cut method according to an embodiment of the present disclosure.

For the endocardium, the method determines the cycle with a maximum confidence. FIG. 5a shows an example of a confidence image. A graph, for example, as illustrated in FIG. 5c, is defined where each node corresponds to connected component regions, as shown in FIG. 5b, between confidence pixels on the candidate contours. The weight of an edge between two nodes is inversely proportional to the confidence of pixels on the common boundary. Then, the method determines a minimum cut between the center node and the outside node. A max flow method is used to determine the minimum cut. FIG. 5d shows an example of a final segmentation, or myocardium contour (shown in dark).

For the epicardium, the method needs a smooth contour since there is no clear edge between the myocardium and the liver, and the right ventricle myocardium appears to merge into the left ventricle myocardium. Therefore, the method fits a spline to the points of the two candidate contours. Spline curves originate from flexible strips used to create smooth curves. Like Bezier curves, splines are formed from piecewise approximations of cubic polynomial functions with zero, first and second order continuity. B-Splines are an example of a particular type of spline.

In order to test our algorithm, we have collected 29 patient data sets along with a manual segmentation of the ED and ES phases by radiologists, for a total of 458 segmented images. The images were acquired on Siemens MAGNETOM systems using two different pulse sequences. FLASH pulse sequences were traditionally used for MR cineangiography. Siemens recently pioneered the TrueFISP pulse sequences for cardiac cine imaging which present higher contrast-to-noise ratio without affecting temporal or spatial resolution. We collected 22 TrueFISP patients and 7 FLASH patients. Our database presents a great variety of heart shapes, image contrast, and edge crispness. The difficulty with FLASH images is that the edges can be blurred. The challenge with TrueFISP images is that the papillary muscles are so well defined that it can be difficult to avoid outlining them. Further, the user may not want to outline them and the shape constraint can help in this task.

Figure 6:
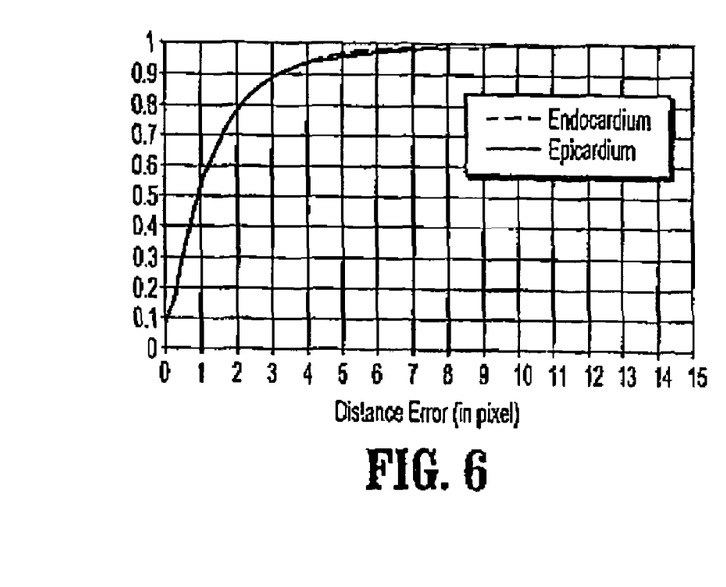
FIG. 6 is a graph showing a cumulative distribution of error distances between true contours and segmented contours for MR images, over all points, over all images, and over all patients.

The method automatically segments ED and ES phases of all the datasets. To compare the automatic contours A with the true contours B, the method determines the distances $d(a,B) = \min_{b \in B} \|a-b\|$ for all points a in the automatic contour. The method also determines $d(b,A)$ for all points b in the true contour. FIG. 6 shows the cumulative distribution of these error distances over all ED and ES images of all 29 datasets. It can be seen that, on the average, the error is less than one pixel and an error of five pixels or more is made less than five percent of the time.

The present disclosure proposes a method for segmenting the left ventricle in cardiac MR images. The method combines edge information, region information obtained from an EM fitting of a mixture of Gaussians to a histogram, and shape information through a point pattern matching strategy. The method can be integrated into, for example, the ARGUS cardiac analysis package from Siemens.

In addition to cardiac MR images, embodiments of the present disclosure are extendable to Computed Tomographic (CT) images. For example, for global localization of a left ventricle, in the case of single image segmentation and ED propagation, an automatic localization technique is used for MR and CT images. For MR images a maximum discrimination method may be used. For CT images, a thresholding method may be used. For ES and temporal propagation a contour is copied or scaled from the previous image.

For CT images, the detection task uses grey level values of the tissue approximately known through the physics of acquisition (e.g., X-rays). The grey levels in the images are stored. Blood pixels are isolated by thresholding. The threshold may be determined from the training examples and may be based on a unit of measure implemented by the CT scanner or cardiac analysis package. For example, grey levels for Siemens CT images is 1024+Hounsfield Unit (HU), where HU is directly output be the CT scanner and air is −1000HU and bone is 1000HU. Thus, a threshold for eliminating blood pixels may be 1211. After removing connected components below the threshold, features for each remaining connected component are determined. For example, the eccentricity is the ratio between the minimum and the maximum radii on the connected component; the convexity is the ratio between the area of the connected component and the area of the connected component hull; and the circularity of the convex hull is defined as $4\pi$ times its area over the square of its perimeter. A connected component that is least eccentric, most circular, and most convex is sought based on these determined features. A connected component that is least eccentric, most circular, and most convex is approximated as a circle and corresponds to a localization of the endocardium. A localization of the epicardium is determined as a circle with the same center and a larger radius as the circle for the endocardium. The larger radius may be selected as a predetermined number of pixels, or other measurement unit e.g., millimeters, larger than the endocardium, for example, 10 pixels larger. Other methods for selecting the larger radius may be used, for example, manual selection.

For ED propagation in CT images, scaling is used. For CT images, a whole volume is acquired at once and therefore there is no shift between slices. Scales are chosen accordingly, for example, both endocardium and epicardium may be scaled by 0.8 down the slices and by 1.25 up the slices.

Figure 7A:
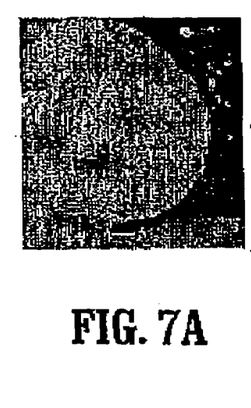
FIG. 7a shows an input image according to an embodiment of the present disclosure.
Figure 7B:
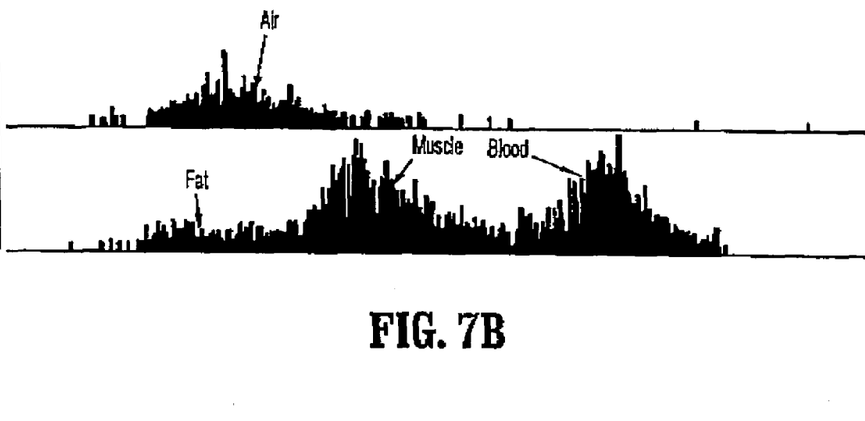
FIG. 7b shows a histogram of the input image of FIG. 7a, fitted with a mixture of Gaussians according to an embodiment of the present disclosure.
Figure 7C:
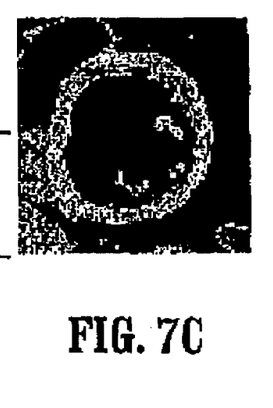
FIG. 7c shows a myocardium response image according to an embodiment of the present disclosure.

For region segmentation of CT images the grey level distribution varies, typically from 100 to 1600, whereas for MR images grey levels vary from about 0 to 700. A histogram (see FIG. 7b) of a CT image (see FIG. 7a) shows four peaks: the lungs are dark and well separated from the other organs. Among the brighter pixels, there is fat and portions of the liver, muscle and blood. The EM method is used to fit four Gaussians to the histogram. The physics of the CT acquisition allowed an average myocardium grey level to be determined empirically. A Gaussian is chosen having a peak closest to the average myocardium grey level. The myocardium response image (see FIG. 7c) is then determined according to a probability that a pixel belongs to the middle Gaussian distribution.

Figure 8:
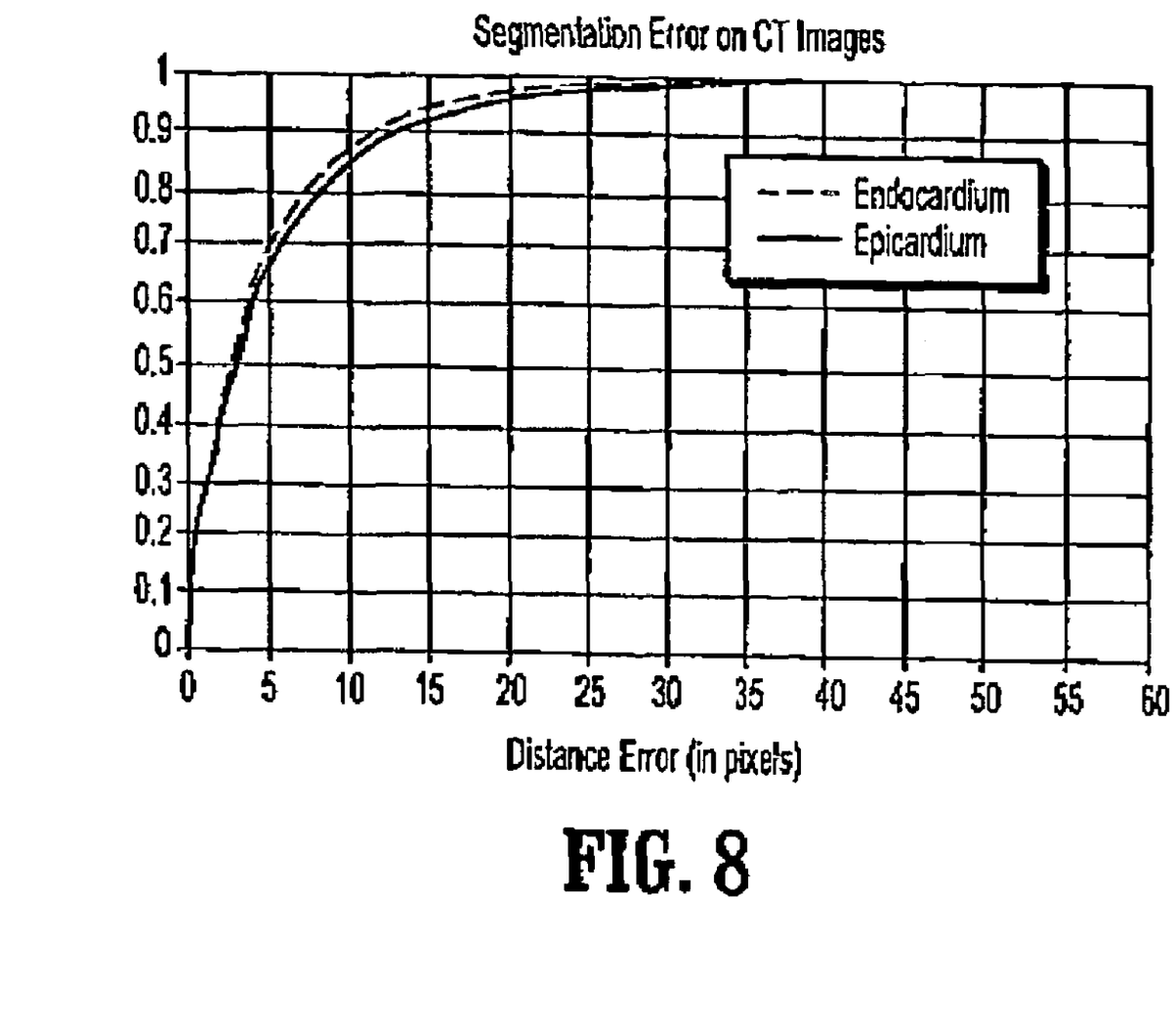
FIG. 8 is a graph showing a cumulative distribution of error distances between true contours and segmented contours for CT images, over all points, over all images, and over all patients.

FIG. 8 shows the cumulative distributions for the error distances for CT images. The average error shown in FIG. 8 is 2.5 pixels. For 95% of the contour points, the error is less than 15 pixels. While the error in CT images appears to be worse than for the MR images (e.g., compare FIG. 6 and FIG. 8), the physical size of a pixel in an MR image is about 3 times larger than in a CT image. Therefore, the performance of the system and method is approximately the same for MR and CT images.

Having described embodiments for cardiac segmentation combining edge, region and shape information in a deformable template, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

What is claimed is:

1. A method for segmenting an image of interest of a cardiac chamber comprising:
   determining a myocardium response image according to a histogram of pixel intensity in the image of interest;
   determining a plurality of candidate contours, according to a plurality of energy functions and the myocardium response image, wherein each of the plurality of candidate contours is assigned a confidence value, wherein the confidence value is determined at every pixel along the candidate contours; and
   determining whether shape information exists for shape propagation,
   wherein the confidence values are modified upon determining that no shape information exists to recover a candidate endocardium contour according to a distance from a center mass of the confidence values of the pixels, wherein the candidate endocardium contour outlines a myocardium contour according to modified confidence values, and to recover a candidate epicardium contour according to the candidate endocardium contour, and
   wherein the myocardium contour is recovered in the presence of shape information by propagating the shape information weighted by the confidence values at each pixel by applying a plurality of shape constraints to the candidate endocardium contours and the candidate epicardium contours, the shape information comprising the candidate endocardium contours and the candidate epicardium contours.

2. The method of claim 1, wherein the myocardium contour is based on a plurality of images in a sequence including the image of interest, wherein the myocardium contour includes an endocardium contour and an epicardium contour.

3. The method of claim 1, further comprising determining an approximate contour pair of the cardiac chamber comprising:
   removing a connected component below a grey level threshold; and
   determining features of a connected component above the grey level threshold.

4. The method of claim 3, further comprising:
   determining the connected component that is least eccentric, most circular, and most convex among a plurality of connected components above the grey level threshold;
   approximating the determined connected component as a circle corresponding to a localization of the endocardium; and
   determining a localization of the epicardium as a circle with the same center and a larger radius as the circle corresponding to the localization of the endocardium.

5. The method of claim 1, wherein determining the myocardium response image according to the histogram of pixel intensity further comprises fitting a mixture of Gaussians to the histogram of pixel intensity to determine portions of blood, muscle and air in the image of interest.

6. The method of claim 1, wherein for each candidate contour, the method further comprises:
   defining a search space around an approximate contour;
   defining a line of source nodes and sink nodes;
   determining a shortest path between the source nodes and the sink nodes;
   defining a new source node and a plurality of new sink nodes; and
   determining a shortest path between the new source node and new sink nodes.

7. The method of claim 1, wherein the candidate endocardium contours and the candidate epicardium contours are each determined according to a combination of a gradient magnitude and a direction using a cross product of a gradient direction and a contour direction.

8. The method of claim 7, further comprising:
   determining a first candidate endocardium contour according to a positive cross product of a gradient direction in the image of interest and a contour direction;
   determining a second candidate endocardium contour according to a negative cross product of a gradient direction in the myocardium response image and a contour direction;
   determining a first candidate epicardium contour according to a gradient magnitude in the image of interest; and
   determining a second candidate epicardium contour according to a positive cross product of a gradient direction in the myocardium response image and a contour direction.

9. The method of claim 1, further comprising determining a one-to-one match matrix, wherein points on the endocardium contour and epicardium contour are assigned to a plurality of template points, wherein the template points are determined from a previous image during propagation through a plurality of images.

10. A method for segmenting an image of interest of a cardiac chamber comprising:
    determining a myocardium response image according to a histogram of pixel intensity in the image of interest, wherein the myocardium response image is a region based segmentation;
    determining a plurality of candidate contours, according to a plurality of energy functions and the myocardium response image, to which a plurality of confidence values are assigned, wherein the plurality of candidate contours correspond to edge information, wherein the confidence values are determined at every pixel along the candidate contours; and
    determining whether shape information is available for the image of interest, wherein, in the absence of shape information, a myocardium contour is determined according to a graph cut of candidate endocardium contours of the plurality of candidate contours, wherein the candidate endocardium contours outline a myocardium contour according to modified confidence values, and a spline fitting to candidate epicardium contours of the plurality of candidate contours according to the candidate endocardium contours having the modified confidence values, and
    wherein, in the presence of shape information, the candidate endocardium contours and the candidate epicardium contours are matched to a template determined by shape propagation weighted by the confidence values at every pixel along the candidate endocardium contours and the candidate epicardium contours through a plurality of images in a sequence including the image of interest, to determine the myocardium contour, wherein the myocardium contour includes an endocardium contour and an epicardium contour from among the candidate contours.

11. The method of claim 10, further comprising determining a contour pair of the cardiac chamber.

12. The method of claim 11, further comprising:
determining a feature of a connected component, the connected component being differentiated from non-cardiac tissue;
determining the connected component having a desirable feature value among a plurality of connected components differentiated from non-cardiac tissue;
approximating the determined connected component as a circle corresponding to a localization of the endocardium; and
determining a localization of the epicardium as a circle with the same center and a larger radius as the circle corresponding to the localization of the endocardium.

13. The method of claim 10, wherein determining the myocardium response image according to the histogram of pixel intensity further comprises fitting a mixture of Gaussians to the histogram of pixel intensity to determine portions of blood, muscle and air in the image of interest.

14. The method of claim 10, wherein for each candidate contour, further comprises:
defining a search space around an approximate contour;
defining a line of source nodes and sink nodes;
determining a shortest path between the source nodes and the sink nodes;
defining a new source node and a plurality of new sink nodes; and
determining a shortest path between the new source node and new sink nodes.

15. The method of claim 10, wherein the candidate endocardium contour and the candidate epicardium contour are each determined according to a combination of a gradient magnitude and a direction using a cross product of a gradient direction and a contour direction.

16. The method of claim 15, further comprising:
determining a first candidate endocardium contour according to a positive cross product of a gradient direction in the image of interest and a contour direction;
determining a second candidate endocardium contour according to a negative cross product of a gradient direction in the myocardium response image and a contour direction;
determining a first candidate epicardium contour according to a gradient magnitude in the image of interest; and
determining a second candidate epicardium contour according to a positive cross product of a gradient direction in the myocardium response image and a contour direction.

17. The method of claim 10, wherein the graph cut further comprises:
defining a graph wherein each node corresponds to a connected component region between the modified confidence values on the candidate contours; and
determining a minimum cut between a center node and an outside node.

18. The method of claim 10, wherein the spline fitting further comprises fitting a spline through points of the candidate epicardium contours.

19. A computer readable medium embodying a program of instructions executable by a processor to perform method steps for segmenting an image of interest of a cardiac chamber, the method steps comprising:
determining a myocardium response image according to a histogram of pixel intensity in the image of interest, wherein the myocardium response image is a region based segmentation;
determining a plurality of candidate contours, according to a plurality of energy functions and the myocardium response image, to which a plurality of confidence values are assigned, wherein the plurality of candidate contours correspond to edge information, wherein the confidence values are determined at every pixel along the candidate contours; and
determining whether shape information is available for the image of interest,
wherein, in the absence of shape information, a myocardium contour is determined according to a graph cut of candidate endocardium contours of the plurality of candidate contours, wherein the candidate endocardium contours outline a myocardium contour according to modified confidence values, and a spline fitting to candidate epicardium contours of the plurality of candidate contours according to the candidate endocardium contours having the modified confidence values, and
wherein, in the presence of shape information, the candidate endocardium contours and the candidate epicardium contours are matched to a template determined by shape propagation weighted by the confidence values at every pixel along the candidate endocardium contours and the candidate epicardium contours through a plurality of images in a sequence including the image of interest to determine the myocardium contour, wherein the myocardium contour includes an endocardium contour and an epicardium contour from among the candidate contours.

* * * * *